United States Patent [19]

Spanton et al.

[11] Patent Number: 4,759,368

[45] Date of Patent: Jul. 26, 1988

[54] TRANSCUTANEOUS NERVE STIMULATOR

[75] Inventors: John B. Spanton, Sunbury; Gregory A. Todd; John P. Landino, both of Westerville; Terry A. Todd, Canton; Richard J. Fisher, Jr., Sunbury, all of Ohio

[73] Assignee: Medical Designs, Inc., Westerville, Ohio

[21] Appl. No.: 936,828

[22] Filed: Dec. 2, 1986

[51] Int. Cl.⁴ .............................................. A61N 1/36
[52] U.S. Cl. .................................................... 128/421
[58] Field of Search ...................... 128/421, 422, 423 R

[56] References Cited

U.S. PATENT DOCUMENTS 4,210,151 7/1980 Keller, Jr. ............................ 128/421
4,340,063 7/1982 Maurer ................................ 128/421
4,431,002 2/1984 Maurer et al. ...................... 128/422
4,453,548 6/1984 Maurer et al. ...................... 128/421
4,580,570 4/1986 Sarrell et al. ....................... 128/421

Primary Examiner—Lee S. Cohen
Attorney, Agent, or Firm—Patrick P. Phillips

[57] ABSTRACT

A transcutaneous nerve stimulating device is provided having a plurality of operating modes, namely burst, normal (single amplitude/single pulse width), rate modulation, amplitude modulation and strength-duration/-rate modulation. In the lattermost mode, the rate modulation control circuitry acts independently of the interrelated amplitude and pulse width modulations to result in a means of nerve stimulation obviating the phenomenon of accommodation.

15 Claims, 3 Drawing Sheets

TRANSCUTANEOUS NERVE STIMULATOR

FIELD OF THE INVENTION

This invention relates to transcutaneous nerve stimulation and more particularly to a transcutaneous nerve stimulating device which represents an advancement in the suppression of organic pain.

BACKGROUND OF INVENTION

This invention is directed to the providing of a transcutaneous nerve stimulator which is designed to be utilized in T.E.N.S. (Transcutaneous Electrical Nerve Stimulation) therapy. T.E.N.S. therapy is based on a non-invasive, non-narcotic concept of pain management which is non-addictive, is not subject to abuse, and does not interact with drugs. T.E.N.S. therapy has already proven to be an effective modality in treating the organic pain problems associated with the following conditions: chronic lumbar and cervical strains or sprains, degenerating disc disease, degenerative arthritic disease, neuropathies, neuralgias, post-lumbar laminectomy syndrome, post-thoracotomy syndrome, bursitis, postphlebitis syndrome, phantom limb syndrome, and tension and migraine headaches.

Early attempts to suppress organic pain and other neurophysical effects utilizing electrical stimulation occurred as early as about 2,000 years ago when it was discovered that gout apparently could be successfully treated by placing the diseased extremities in a tub of water filled with electric eels. Later, headaches were treated using a similar approach. A detailed, scientific investigation was finally conducted by Professor Galvani of the University of Bologna, which investigation is credited with ultimately leading to the development in the 1800's of electical equipment for suppression of organic pain.

The earliest therapeutic devices utilizing electrical simulation for the most part featured a constant amplitude and rate. Examples of the early art are Benz, U.S. Pat. No. 646,793; Raymond et. al., U.S. Pat. No. 872,148; Tibbals, U.S. Pat. No. 1,059,090; and Call, U.S. Pat. No. 1,908,688. A major problem with electrical stimulation therapy was, and still is, accommodation, whereby the nerve being stimulated in effect accommodates itself over time to the electrical charge, such that the effectiveness of the treatment is diminished.

It took scientists a long time to discover, and attempt to address the problem. Nemec, U.S. Pat. No. 2,622,601; DiPerna, U.S. Pat. No. 2,624,342; and Gratzl, U.S. Pat. No. 2,771,554 all disclose electrotherapeutic devices with at least one including means to vary the rate, amplitude or pulse width of the generated electrical pulse. However, merely being able to change either the rate, amplitude or pulse width still resulted in the problem of accommodation occurring, unless an individual manually adjusted the controls prior to the occurrence of accommodation. The process was both labor intensive and inefficient, with respect to the quality of the therapy, since maximum pain relief was not being provided.

In 1967, a Dr. Sweet at Massachusetts General Hospital developed the first T.E.N.S. unit. The effectiveness of T.E.N.S. therapy is based on its incorporating two major pain control theories. Under the so-called Gate Control Theory, pain can be inhibited and suppressed by "closing the gate" on pain signals as such signals arrive at Central Nervous System centers. This theory postulates that by providing electrical stimulation of a sufficiently high amplitude, the electrical signals race up large myelinated fibers faster than the pain signals travel up smaller myelinated or unmyelinated fibers. The neutral impulses transmitting pain information to the brain thus become interrupted, and since the brain fails to receive the pain signals, no pain is perceived. The other theory incorporated in T.E.N.S. units is the Endorphin Theory, also known as the Endogenous Opiate Theory. This theory postulates that the sustained input of T.E.N.S. signals triggers the release of naturally occurring pain making endorphins and enkephalins (morphine-like substances). These natural substances seemingly block pain signals by a mechanism similar to conventional drug therapy, and inhibit pain information from reaching the brain.

However, T.E.N.S. units, like all electrotherapeutic devices, have suffered problems with accommodation. For example, Geerling, U.S. Pat. No. 4,019,519 issued in 1977, disclosed a unit having only its amplitude adjustable. Miller, U.S. Pat. No. 4,084,595 issued in 1978, disclosed a unit having its rate, amplitude, and pulse width all independently, manually adjustable. However, even this advancement resulted in a less than efficient treatment of the problem of accommodation, since either the therapist or the patient had to, in theory, repeatedly adjust the controls in an attempt to avoid accommodation.

Although variation enables one to deal with the problem of accommodation, pain relief is sacrificed. This is in part due to the interaction between amplitude and pulse width. There is a clinical correlation between amplitude and pulse width with regard to the efficacy of the stimulus. As one shortens the duration of a pulse, its amplitude must be increased to maintain the efficacy of the stimulus. This relationship when plotted graphically is known as a strength-duration curve. Thus not only must the ideal T.E.N.S. units have adjustable amplitude and pulse width, but it must also be able to modulate those values in such a way as to approximate the A-gamma-motor strength-duration curve.

In addition to amplitude and pulse width approximating the strenght-duration curve, the rate of the pulses must vary so as to eliminate any potential for accommodation. This explains the short-comings in Reiner, U.S. Pat. No. 2,808,826 which disclosed a unit which permitted instantaneous changes in pulse width and amplitude to two pre-set points along the strength-duration curve, and Maurer, U.S. Pat. No. 4,340,063 which disclosed a unit having its amplitude modulate in response to modulations in pulse width so as to approximate a portion of the strength-duration curve. The rate in Maurer was adjustable, but only to the extent taught by Miller, such that the problem with accommodation still existed.

SUMMARY OF THE INVENTION

In accordance with this invention, a transcutaneous nerve stimulator is provided for advantageous use in T.E.N.S. therapy. In accordance with this invention, the amplitude, pulse width and rate all modulate with respect to one another so as to obviate any potential for the phenomenon of accommodation.

Included in the stimulator are a plurality of circuits, designed such that the unit may operate in any one of five modes: burst, conventional single amplitude/single pulse width, rate modulated, amplitude modulated, and strength-duration/rate modulated. In this final mode, the coordinated amplitude and pulse width approximate the selected nerve's strength-duration curve. A Schmidt Trigger serves to generate pulses, with at least one of the controls for amplitude, pulse width and rate being independently adjustable for the first four modes and with all three control means having their respective values modulate when in the fifth mode. In this fifth mode the amplitude control means and pulse width control means are electrically coupled, with the rate control means interacting with the product of the coupling, so as to provide maximum sensory stimuli and maximum pain relief while eliminating the phenomenon of accommodation.

The primary objective of this invention is to provide a nerve stimulating device for use in T.E.N.S. therapy that eliminates the phenomenon of accommodation. Important aspects of this objective are the approximation of a nerve's strength-duration curve and the additional effect caused by having the rate modulated so as to interact with the curve generated by the interaction of amplitude and pulse width.

Another object is the providing of a T.E.N.S. unit which can provide a plurality of operating modes, including one for strength-duration/rate. This important objective is furthered by the providing of several circuits and selectively adjustable mode control means which permits any one of five operating modes to be chosen.

Still another objective is to provide a T.E.N.S. unit having all the capabilities of this invention that is of extremely economical construction and is particularly easy to operate. This objective is furthered by supplying a T.E.N.S. unit having all the chartacteristics of this invention as a portable, handheld unit.

These and other objects and advantages of this invention will be readily apparent from the following detailed description of an illustrative embodiment thereof. Reference will be had to the accompanying drawings which illustrate the embodiment of the invention.

DESCRIPTION OF THE DRAWING FIGURES

DESCRIPTION OF THE ILLUSTRATIVE EMBODIMENT

Figure 1:
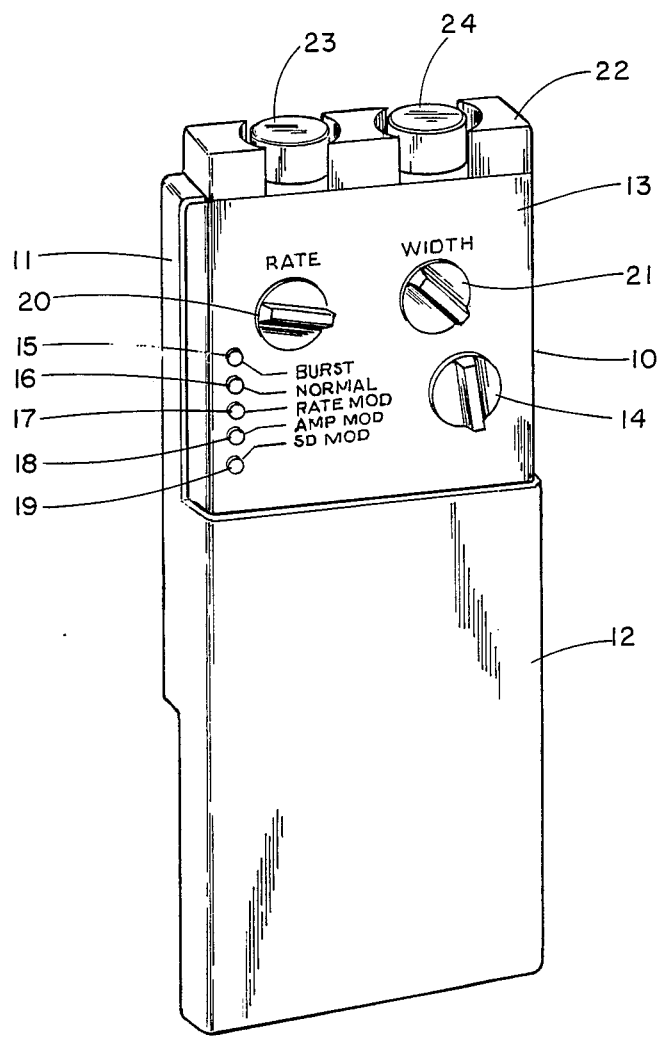
FIG. 1 is a perspective view of a transcutaneous nerve stimulator in its operative condition, showing the various controls.

Having reference to the drawings, attention is directed first to FIG. 1 which illustrates a transcutaneous nerve stimulator embodying this invention and designated generally by the numeral 10. This T.E.N.S. unit 10 has a base 11 and cover 12 which are slidably interconnected, such that when the unit is in use the cover 12 is slidably displaced to reveal front display panel 13. The front display panel 13 features several adjustable control means. Mode selector 14 permits the unit 10 to operate in five distinct modes. Indicator lights 15,16,17,18, and 19 correspond to burst, normal or conventional single amplitude/single pulse width, rate modulated, amplitude modulated and strength-duration/rate modulated modes, with a specific light being activated in response to the mode selected. The indicator lights permit the user to know what mode the unit 10 is in for reasons of safety. Also on the front display panel 13 are rate and pulse width control means 20 and 21 respectively.

The unit 10 also features a top display panel 22 featuring two amplitude control means 23 and 24, each of which are associated with an electrode which is attached to the skin of the patient. Electrode outlets (not shown) are located on the base 11 adjacent to the rear of top display panel 22. Also located there is a low battery light (not shown) which serves to apprise the user of the charge conditions of the energy source used to power the transcutaneous nerve stimulator of this invention.

Figure 2:
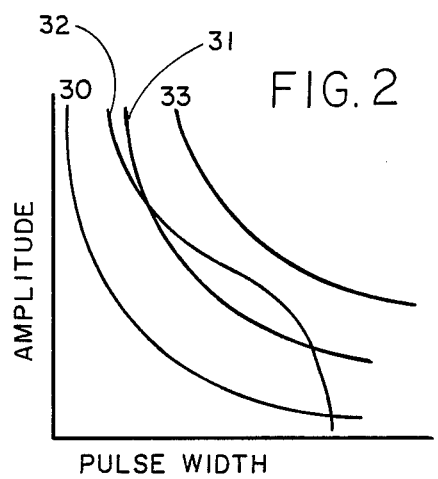
FIG. 2 is a diagram of strength-duration curves for various classes of nerve fibers.

Referring to FIG. 2, sensory, motor and pain thresholds are illustrated by strength duration curves 30, 31, 32 and 33. Each curve shows the effect of a specific pulse width and amplitude on the firing of a particular class of nerves. When the A-alpha-beta-sensory curve is intersected, that class of nerves experiences a tingling sensation due to the current flow through those nerves. When the A-gamma-motor curve is intersected, that class of nerves experiences muscle fasciculation. When the a-delta-pain or C-fibers-pain curves are intersected, those classes of nerves experience discomfort which the individual perceives as pain. The horizontal coordinate is a measurement of stimulus pulse width, while the vertical coordinate is a measurement of stimulus amplitude. Curve 30 corresponds to the A-alpha-beta-sensory curve. Curve 31 corresponds to the A-gamma-motor curve. Curve 32 corresponds to the A-delta-pain curve. Curve 33 corresponds to the C-fibers-pain curve. Ideally the level of stimulation should be just below the level of muscle fasciculation (the A-gamma-motor curve) as well as below the level of any pain.

Figure 3:
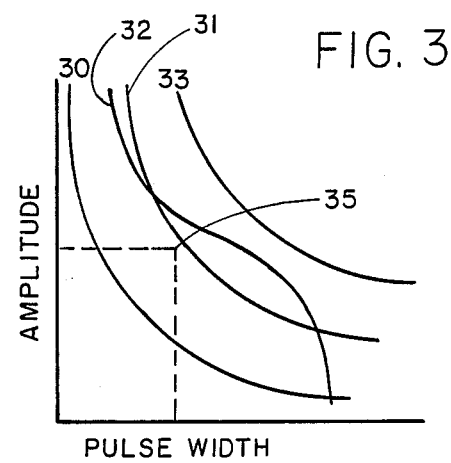
FIG. 3 is a diagram similar to FIG. 2 but showing the phenomenon of accommodation.

As shown in FIG. 3, a T.E.N.S. unit may be adjusted to generate pulses having a single amplitude and single pulse width 35 at a level of ideal stimulation. However, with extended use, problems occur due to accommodation. The phenomenon of accommodation results in the nerve being stimulated requiring a greater degree of stimulation as time passes, due to the nerve become depolarized and hence less sensitive to stimuli.

Figure 4:
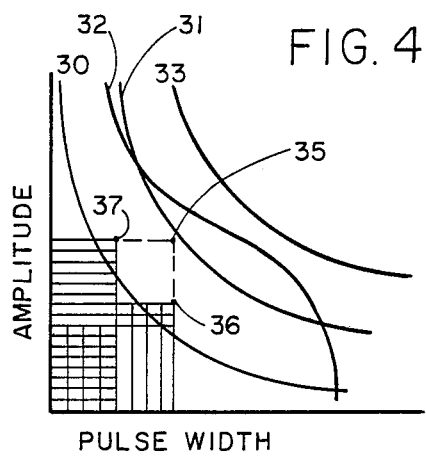
FIG. 4 is a diagram showing the effect of conventional modulation of either amplitude or pulse width.

One way to deal with the problem of accommodation has traditionally been to modulate either the amplitude or the pulse width in a decreasing fashion as shown in FIG. 4. By decreasing the amplitude from that of point 35 to point 36, or by decreasing the pulse width from that of point 35 to point 37, the problem of accommodation is lessened, however the efficiency of the pain suppression is also compromised.

Figure 5:
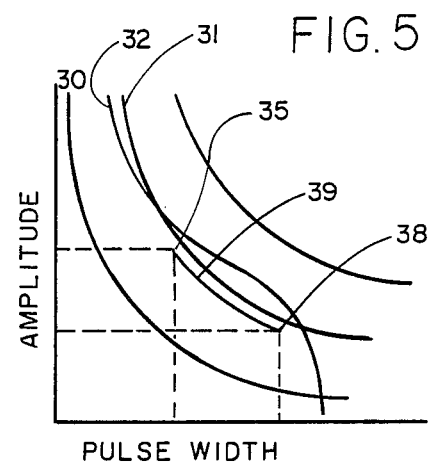
FIG. 5 is a diagram showing the effect of strength-duration modulation.

According to this invention, a T.E.N.S. unit is provided which can operate in a burst mode, the three modes shown in FIGS. 3 and 4 plus in a fifth mode wherein the phenomenon of accommodation is obviated. In this new mode the amplitude and pulse width modulate from point 25 to point 38 in a predetermined manner such that the values for the amplitude and pulse width when in this mode are shown in curve 39, which approximates the strength-duration curve 31. In this new mode, while the amplitude and pulse width are responding to each other as shown in FIG. 5, the rate of the generated pulses is also modulating. Utilization of the unit 10 in the fifth mode eliminates problems with accommodation since the nerves are allowed to relax and therefore re-polarize.

Now that the general physical and operational features of the apparatus 10 have been described, consideration will now be given to the electrical circuitry used in implementing the preferred embodiment.

Figure 6:
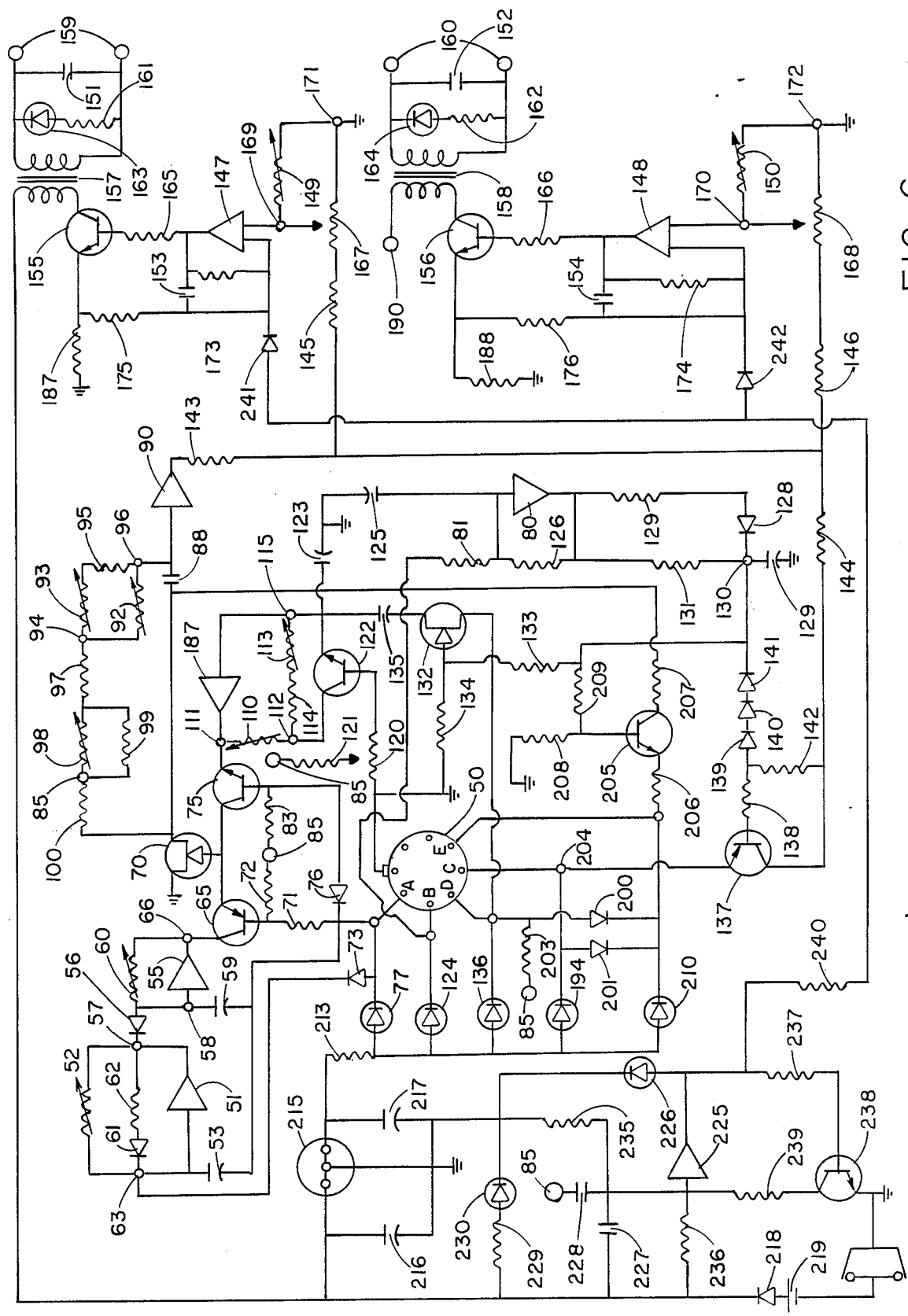
FIG. 6 is a schematic diagram of the circuitry used in the preferred embodiment.

Referring to FIG. 6 the pulses for this invention are generated by five of the gates of a Schmidt Trigger, while the sixth gate toggles a low battery indicator. Choice of which of the five gates are operating is determined by switch 50. When the switch is in position A, the unit 10 is in burst mode. This mode exhibits the same net effect quantitatively and qualitatively as the normal mode setting. However the clinical effect is that fasciculation should occur at lower amplitude settings, thus providing for a comfortable sensation during treatments. Position A utilizes gates 51 and 55. Gate 51 is trimmed to 2 Hz by a 500K resistance trimmer 52. Input into oscillator 51 is driven by a 6.8 mf capacitor 53 such that the resistance capacitance timing network is accomplished by the first trimmer and capacitor.

Coupling from gate 51 to 85 Hz oscillator 55 is achieved by diode 56 located between pins 57 and 58. A capacitor 59 and 10K trimmer 60 allow gate 55 to produce a 85 Hz signal. Both trimmers 52 and 60 are fixed after adjusting them to specified parameters. Diode 61 and 68K fixed resistor between points 63 and 57 insert 7 pulses into gate 55 twice each second.

Transistor switch 65 coupled gate 55 output signal through pin 66 into the gate of field effect transistor 70 when the switch 50 is in position A. Switch position A also puts to ground both capacitors 53 and 59 associated with gates 51 and 55, to activate those two gates of the Schmidt Trigger integrated circuit. Switch position A also grounds the base of pnp transistor 65 through a 68K fixed resistor 71. A 470K fixed resistor 72 located at the base of transistor 65 permits a regulated 5V signal to pass through it when the switch is in position A. When another switch position is used, capacitors 53 and 59 are lifted from ground, thereby closing gates 51 and 55. The presence of diode 73 helps to ensure that when gates 51 and 55 are shut off, the burst signals are prevented from reaching field effect transistor 70. When the switch is not in position A, diode 73 allows a small positive voltage to reach gate 51, holding both it and gate 55 from floating. Diode 73 has no effect on the gates when the switch is in position A, such that the pulse signals reach the gate of transistor 70 via transistor 65. Switch position A also grounds the base of transistor 75 through diode 76, as well as LED 77 which light indicates on the front display panel 13 that the unit is operating in burst mode.

Switch position B permits operation of the unit 10 in the conventional or normal single amplitude/single pulse width mode. In this mode on this unit the rate, amplitude and pulse width all are manually adjustable, however there is no modulation. When the switch 50 is in position B the input of oscillator 80 through 68K fixed resistor 81 is grounded. This prevents oscillator 80 from operating. Preferably this Schmidt Trigger gate uses a 6 second oscillator. In position B the base of transistor 75 is pulled high through 470K fixed resistor 83 on the 5V supply 85, thereby allowing the signal from oscillator 87 to reach the gate of transistor 70.

The pulse width adjustment trimmers to 5V supply 85 are preferably for minimum and maximum parameters of 30 and 225 micro seconds respectively through the network of a 0.001 mf coupling capacitor 88 at the input of gate 90 of the Schmidt Trigger. The 0.001 mf capacitor is driven by the drain of transistor 70, with the pulse rate being coupled to the input of gate 90 through capacitor 88. Pulse width is adjusted by 470K variable resistor 92 after trimming the minimum and maximum parameters. The maximum is adjusted through the use of 500K trimmer 93 or pin 94 through the 330K fixed resistor 95 to pin 96 and thence to gate 90. The minimum is adjusted through the 22K fixed resistor 97 and through the 500K variable and 120 fixed resistors 98 and 99 respectively to the 5V supply 85. A 10K fixed pull-up resistor 100 is located on the 5V supply to the drain of transistor 70.

The rate is trimmed by 10K trimmer 110 located between pins 111 and 112 such that the maximum is 110 pulses per second. The minimum rate is adjusted by a 500K trimmer 113 located between 470K fixed resistor 114 and pin 115, such that the minimum is 1 pulse per second. After setting the minimum and maximum parameters, adjustment to the rate is obtained by a 470K potentiometer 120 with the wiper of said potentiometer 120 through a 56K fixed resistor 121 tied to the 5V supply 85. This variable resistor divider network allows the base of transistor 122 to offset, thereby making it easier to read the values on rate adjustment knob 20. Turning knob 20 results in potentiometer 120 causing a non-linear adjustment to the rate. A 3.3 mf capacitor is located between the emitter of transistor 122 and ground. When the switch 50 is in position B, LED 124 is in an "on" condition, indicating the unit is in the normal mode.

Switch position D permits the 6 second oscillator 80 to again function by lifting from ground the 68K fixed resistor 81, allowing the 6.8 mf capacitor 125 to change the resistance capacitance network at oscillator 80 with a 2M fixed resistor 126 allowing transition between high and low states. Gate 80 of the Schmidt Trigger connects to 180K resistor 127 which is connected to diode 128. This circuit is connected to one having 10 mf capacitor 129 at pin 130. Located between pin 130 and 2 m resistor 126 is 180K resistor 131. Fixed resistors 127 and 131, diode 128 and capacitor 129 slow the transition of gate 80 to allow the gate of field effect transistor 132 to be driven through a 2M resistor 134 tied to ground to deplete the charge of the capacitor 129 as the gate 80 is driven high to low.

When the switch 50 is in position D, transistor 132 adds the 3.3 mf capacitor 135 to gate 87 of the 1 to 110 Hz oscillator, thereby decreasing the rate of the output pulses by approximately 50%, regardless of the setting of potentiometer 120. As the gate 80 transcends from low to high, gate 132 is driven high to low allowing the drain through switch position D to reach ground. The source of transistor 132 with capacitor 135 is added and depleted during the transition of gate 80 from high to low. At gate 87, capacitor 135 is decreasing the rate by approximately 50% followed by its return to the initial rate. Switch position D also grounds LED 136 to an "on" position, thereby indicating that the unit is operating in the rate modulation mode.

Switch position C connects the emitter of transistor 137 to ground. The base of transistor 137 through 47K resistor 138 and three voltage dropping diodes 139, 140 and 141 is driven from high to low from the output of oscillator 80. The 470K fixed resistor 142 on the cathode side of the three diodes 139,140 and 141 is driven from high to low from the output of oscillator 80. The 470K fixed resistor 142 on the cathode side of the three diodes 139, 140 and 141 is a feedback resistor, feeding the base of transistor 137. The collector of transistor 137 also pulls the output signal of gate 90 through 4.7 fixed resistor 143, 3.3 K fixed resistor 144, and the two 56K fixed resistors 145 and 146. The network of the four fixed resistors 143, 144, 145 and 146 decreases the output signal through the two 56K resistors 145 and 145 into the input of the operational amplifiers 147 and 148 respectively by 25%, which is the preferred amount of decrease for this invention.

Amplitude is further controlled by standard feedback loop balanced amplifiers 147 and 148. Output is variable to 60 milliamps through 10K variable resistors 149 and 150 and is clamped at 150V and filtered by 0.0047 mf capacitors 151 and 152. Two 39 pf capacitors 153 and 154 are utilized for noise reduction. Both channels use npn transistors 155 and 156 respectively, with the collector of each transistor connected to transformers 157 and 158 respectively. Between the transformers and the electrode jacks 159 and 160 are 10K resistors 161 and 162 and LEDS 163 and 164. 390 ohm resistors 165 and 166 are located between amplifiers 147, 148 and transistors 155, 156. Adjustability of the amplitude for each electrode channel is controlled by 20K potentiometers 167 and 168, with pins 169 and 170 located between the amplifiers 147, 148 and the potentiometers 167, 168. Also located between variable resistors 149, 150 and potentiometers 167, 168 are pins 171 and 172 which go to ground. Located between the amplifers and the capacitors 153, 154 and 120 K fixed resistors 173 and 174. Between capacitors 153, 154 and the emitters of transistors 155, 156 are 1K fixed resistors 175 and 176. Before going to ground, the current from transistors 155 and 156 passes through 0.27 ohm resistors 187 and 188 respectively. Transformer 158 is provided with a 9V power supply 190. Switch position C also grounds LED 194 to an "on" condition, indicating that the unit is operating in an amplitude modulation condition.

Switch position E results in a mode not heretofore available in T.E.N.S. units. Features of switch positions C and D are incorporated into the circuit associated with position E. A pair of Germanium diodes 200 and 201 connect circuit D to E and C to E respectively, with a 10K fixed pull-up resistor 203 connected to 5V power supply 85 allowing for a current flow to bias the Germanium diodes. Pin 204 is located between switch C and diode 201. The emitter of transistor 205 through 2.2K resistor 206 to position E is to ground. This allows 27K resistor 207 to decrease the 0.001 mf capacitor 88 on the drain of transistor 70 by 40%. This decreases the pulse width by 40% while not altering the rate. The 330K fixed resistor 208 on the base of transistor 205 returns the base to normal when not being high by the output of gate 80 through the 470K resistor 209 to the base. Thus when the unit 10 is in this mode, rate modulation is occurring at the same time as is amplitude/pulse width modulation.

In actual operation the initial component of the 6 second oscillation involves a dramatic 50% decrease in the rate followed by a return of the rate to its initial value during which time the amplitude and pulse width modulate such that as the amplitude decreases by 25% the pulse width increases by 40%. Once point 38 is reached, as the amplitude increases to its initial value the width decreases to its initial setting. Once the amplitude and pulse width have returned to their original settings the next 6 second oscillation occurs. LED 210 when in an "on" position indicates the unit 10 is in the strength duration/rate modulation mode.

LED's 77, 124, 136, 194 and 210 are tied to a 2.2K fixed current limiting resistor 213. Power supply 85 is regulated to 5V by regulator 215. A 330 mf capacitor 216 is directly across the battery potential. Also located in the LED circuit between power supply 85 and regulator 215 is capacitor 217. Diode 218 is adjacent battery 219 and serves to prevent damage to the unit in cases of accidental battery reversal. The final gate 225 activates low battery light LED 226 in cases when the power falls below 5V due to a weakened battery. Preferably this diode will emit a color of light different from the other LEDs.

A 0.033 mf capacitor 227 from the 9V battery 219 initializes gate 225 to pull that gate high, thereby preventing LED 226 from being lighted. A 0.001 mf capacitor 228 from the regulated 5V power supply 85 helps to keep electronic noise from gate 225. Current flow through 10K resistor 229 causes LED 230 to emit preferably a red color thereby providing a signal that the battery has some charge left. However, the occasion may arise Cwhere the power in the battery falls below 6V. In that situation it is safer for the use of the unit to be interrupted and the battery to be replaced.

The interruption occurs when the divide network including 330K and 470K resistors 235 and 236 respectively falls to 6V. At that time the input of gate 225 which is normally high, goes to ground through 20K resistor 237 and transistor 238. Also at this time current through 120K resistor 239 closes gate 225. Once current flows through and closes gate 225, diode 226 becomes lit, in addition to current flowing through 1K resistor 240 to diodes 241 and 242 which are connected to operating amplifiers 147 and 148 respectively. The passage of current through these diodes shuts down the amplifiers, thereby preventing the unit from functioning. This situation continues until the battery is replaced, at which time the input to gate 225 will once again be high, such that no current will be flowing to diodes 241 and 242.

It will be readily apparent, from the foregoing detailed description of the preferred embodiment of this invention, that a particularly novel and extremely effective T.E.N.S. device is provided. This device is relatively simple to fabricate and results in a device which provides a degree of relief heretofore unknown in the treatment of pain.

Having thus described this invention, what is claimed is:

1. A transcutaneous nerve stimulating device which eliminates the phenomenon of accommodation, comprising a pulse generator means for generating a plurality of pulses, interconnected amplitude, pulse width, and rate modulation control means, which cause the amplitude, pulse width and rate of the generated pulse to vary in a prescribed manner, said amplitude control means interacting with said pulse width control means such that a change in the pulse amplitude will effect an inverse change in the pulse width, with pulse width decreasing when pulse amplitude increases and with pulse width increasing when pulse amplitude decreases, said rate modulation control means acting independently of the relationship between said amplitude control means and pulse width control means to modulate the rate of the pulse generated, and means for carrying said pulses to tissue engaging electrodes.

2. A device according to claim 1 wherein said generated pulse is associated with a current flow which is allowed to bias Germanium diodes as part of the circuitry of said device.

3. A device according to claim 1 wherein said amplitude, pulse width and rate control means are electrically connected.

4. A device according to claim 1 wherein said prescribed manner first includes the decreasing of the rate followed by its increase back to the initial rate, and secondly the mutual interaction between the amplitude control means and the pulse width control means such that the pulse width is responsive to changes in amplitude.

5. A device according to claim 4 wherein said rate decreases by 50%.

6. A device according to claim 4 wherein said mutual interaction between said amplitude control means and said pulse width control means causes the pulse width to increase by 40% responsive to a decrease in the amplitude of 25%, followed by their return to their initial values.

7. A device according to claim 6 wherein said mutual interaction results in specific amplitude and pulse width values which if plotted would the approximate A-gamma-motor curve strength-duration associated with the nerve being stimulated.

8. A device according to claim 7 wherein said pulse width increases in response to a decrease in amplitude until said pulse width reaches the A-delta-pain line.

9. A device according to claim 4 wherein said prescribed manner has a modulation cycle of six seconds, said modulation cycle being the time of the rate modulation as well as the mutual interaction between the pulse width control means and the amplitude control means.

10. A device according to claim 1 which includes means for additional modes of operation having pulses generated in other than said prescribed manner, said additional modes including rate modulation, amplitude modulation, single amplitude/single pulse width and burst.

11. A device according to claim 1 wherein the prescribed manner includes decreasing of the rate by 50%.

12. A device according to claim 11 wherein said prescribed manner includes mutual interaction between said amplitude control means and said pulse width control means which causes the pulse width to increase by 40% responsive to a decrease in the amplitude of 25% followed by their return to their initial values.

13. A device according to claim 12 wherein said mutual interaction results in specific amplitude and pulse width values which is plotted would approximate the A-gamma-motor strength duration curve associated with the nerve being stimulated.

14. A device according to claim 13 wherein said pulse width increases in response to a decrease in amplitude until said pulse width reaches the A-delta-pain line.

15. A device according to claim 1 wherein said prescribed manner includes mutual interaction between said amplitude control means and said pulse width control means and has a modulation cycle of six seconds, said modulation cycle being the time of the rate modulation as well as the time involved in the mutual interaction between the pulse width control means and the amplitude control means.

* * * * *

UNITED STATES PATENT AND TRADEMARK OFFICE
CERTIFICATE OF CORRECTION

PATENT NO. : 4,759,368
DATED : July 26, 1988
INVENTOR(S) : Gregory A. Todd et al.

It is certified that error appears in the above-identified patent and that said Letters Patent is hereby corrected as shown below:

Column 9, Claim 7, line 27, "the approximate" should read --approximate the--.

Column 9, Claim 7, line 28, "ma-motor curve strength-duration" should read --ma-motor strength-duration curve--.

Signed and Sealed this

Twenty-ninth Day of November, 1988

Attest:

DONALD J. QUIGG

*Attesting Officer*  *Commissioner of Patents and Trademarks*